(12) United States Patent
Stephan et al.

(10) Patent No.: US 8,349,459 B2
(45) Date of Patent: Jan. 8, 2013

(54) INFILTRATION GLASS CONTAINING NIOBIUM

(75) Inventors: Marc Stephan, Lörrach (DE); Bernhard Durschang, Rottendorf (DE)

(73) Assignee: Vita Zahnfabrik H. Rauter GmbH & Co. KG, Bad Säckingen (DE)

( * ) Notice: Subject to any disclaimer, the term of this patent is extended or adjusted under 35 U.S.C. 154(b) by 360 days.

(21) Appl. No.: 12/532,279

(22) PCT Filed: Mar. 18, 2008

(86) PCT No.: PCT/EP2008/053247
§ 371 (c)(1),
(2), (4) Date: Jan. 15, 2010

(87) PCT Pub. No.: WO2008/113810
PCT Pub. Date: Sep. 25, 2008

(65) Prior Publication Data
US 2010/0112331 A1    May 6, 2010

(30) Foreign Application Priority Data

Mar. 22, 2007 (EP) .................... 07104702

(51) Int. Cl.
*B32B 17/06* (2006.01)
*B32B 9/00* (2006.01)
*B32B 15/00* (2006.01)
*C03C 3/097* (2006.01)
*C03C 3/062* (2006.01)

(52) U.S. Cl. .......... 428/428; 428/426; 428/432; 501/63; 501/73

(58) Field of Classification Search .................... 501/63, 501/73, 77–79; 428/426, 428, 432
See application file for complete search history.

(56) References Cited

U.S. PATENT DOCUMENTS

| | | | | |
|---|---|---|---|---|
| 3,958,999 | A | * | 5/1976 | Izumitani et al. ............... 501/51 |
| 4,437,192 | A | * | 3/1984 | Fujiu et al. .................. 623/23.56 |
| 6,346,493 | B1 | * | 2/2002 | Kniajer et al. .................. 501/17 |
| 7,816,292 | B2 | * | 10/2010 | Zimmer et al. .................. 501/11 |

FOREIGN PATENT DOCUMENTS

| | | |
|---|---|---|
| DE | 69206256 T2 | 7/1996 |
| DE | 10061630 A1 | 6/2002 |
| EP | 0241384 A2 | 10/1987 |
| WO | 2005115936 A2 | 12/2005 |
| WO | WO-2005/115936 A2 * | 12/2005 |

OTHER PUBLICATIONS

In Computational Modelling of Materials, Minerals and Metals Processing, edited by M. Cross, J.W. Evans and C. Bailey, TMS (The Minerals, Metals & Materials Society), 2001, Anil Saigal et al. (XP-008082072).

* cited by examiner

*Primary Examiner* — Noah Wiese
(74) *Attorney, Agent, or Firm* — Dardi & Herbert, PLLC; Curtis B. Herbert

(57) ABSTRACT

The present invention relates to an all-ceramic dental prosthesis in which a porous ceramic matrix material is infiltrated with a glass, having a solubility of $<1100\,\mu g/cm^2$ according to DIN EN ISO 6872. The invention also relates to the use of niobium-containing glass having an $Nb_2O_5$ content of more than 0.1% by weight as an infiltration glass for all-ceramic dental compositions.

18 Claims, No Drawings

INFILTRATION GLASS CONTAINING NIOBIUM

RELATED APPLICATION

This application is a national stage filing of PCT Application No. PCT/EP2008/053247 filed Mar. 18, 2008, which claims priority to European Patent Application No. 07104702.1 filed Mar. 22, 2007, each of which are hereby incorporated herein by reference.

1. Technical Field of the Invention

The present invention relates to a niobium-containing infiltration glass, especially for ceramic bodies, and a ceramic body employable as an all-ceramic dental prosthesis in which a porous ceramic matrix material is infiltrated with a glass.

2. Introduction to the Invention

Today, all-ceramic compositions are employed in the frontal tooth region, as inlays, onlays, veneers and posterior fixed partial dentures.

EP-B-0 241 384 describes a process in which metal oxide particles are sintered with open pores, and the infrastructure thus obtained is subsequently infiltrated with a glass. The sintered infrastructure mainly consists of alumina and/or zirconia. An alkaline borosilicate glass containing alumina is described as an infiltration glass. In the Examples, lanthanum oxide is one of the main components of the glass. The expansion coefficient is to be slightly below that of the porous infrastructure.

DE-B-100 61 630 discloses a process in which cerium-stabilized zirconia and mixtures of cerium-stabilized zirconia with alumina are used as a matrix material. In addition, a glass having a composition of 15-35% by weight $La_2O_3$, 10-25% by weight $SiO_2$, 10-25% by weight $Al_2O_3$, 5-20% by weight $B_2O_3$, 5-20% by weight CaO, 0-10% by weight $ZrO_2$, 0-10% by weight $TiO_2$ and 0-15% by weight $CeO_2$ is claimed, as well as additions of further $ZrO_2$-stabilizing metal oxides, especially 0-10% by weight MgO and 0-10% by weight $Y_2O_3$.

Further, DE 692-T-06 256 describes matrix materials based on alumina/magnesia spinels.

WO-A-2005/115936 relates to a glass or glass ceramic powder comprising multicomponent glasses with at least three elements characterized in that the glass or glass ceramic powder has a mean particle size of <1 µm, preferably <0.1 µm, more preferably <10 nm. Disclosed are glass compositions of 5% by weight $SiO_2$, 20% by weight $B_2O_3$, 2.5% by weight $TiO_2$, 2.5% by weight $ZrO_2$, 20% by weight ZnO, 35% by weight $La_2O_3$, 5% by weight $WO_3$ and 10% by weight $Nb_2O_5$, designed for use in the field of infiltration glasses and dental ceramics. In Computational Modelling of Materials, Minerals and Metals Processing, edited by M. Cross, J. W. Evans and C. Bailey, TMS (The Minerals, Metals & Materials Society), 2001, Anil Saigal et al. describe infiltration glasses of $La_2O_3$—$Al_2O_3$—$B_2O_3$—$SiO_2$ in which niobium is not contained.

DESCRIPTION OF THE INVENTION

It is the object of the invention to develop a glass that can be infiltrated into the known all-ceramic matrices and has improved mechanical and chemical stabilities. The glasses employed to date are limited by various boundary conditions. The infiltration temperature must be below the sintering temperature of the matrix, best below 1200° C. The expansion coefficient must be slightly below that of the matrix. The glass must not have an undesirable color. It must be possible to infiltrate the glass flawlessly. The glass is to have high mechanical and chemical stabilities. It is especially the limitation of the infiltration temperature and thus the viscosity of the glass-forming melt that conflicts with the chemical and mechanical stability, since glasses having a high proportion of network formers (e.g., $SiO_2$, $B_2O_3$) have very good mechanical and chemical stabilities, but reach the required viscosity of about $10^3$ dPas only at elevated temperatures.

Although the high lanthanum glass used to date can be filtrated excellently and exhibits good mechanical properties when exactly matched in terms of expansion behavior, it is sufficient only as a matrix material in the field of chemical stability within the meaning of dental standards.

Surprisingly, it has been found that the use of niobium oxide both as an additive to lanthanum-containing glasses and as a component in other silicate systems provokes a significant improvement in chemical stability. The object of the invention is achieved by a silicate-based infiltration glass for ceramic bodies wherein said infiltration glass contains niobium in greater than naturally occurring quantities. In the infiltration glasses according to the invention, the Nb may occur in amounts of at least 0.1% by weight, calculated as $Nb_2O_5$ and based on the total amount of the infiltration glass. In particular, the system $SiO_2$—$Nb_2O_5$—$Na_2O/K_2O$, for example, can have from 10 to 70% by weight $SiO_2$, from 1 to 40% by weight $Na_2O/K_2O$ and from 1 to 60% by weight $Nb_2O_5$.

The infiltration glass according to the invention showed a reduction in glass solubility to below 3% of that of the known glasses when aged as a defined glass grit (grain fraction 100-200 µm, by analogy with DIN ISO 719) in 4% acetic acid at 80° C. for 16 hours. The mechanical properties and the further specifications are not adversely affected by the niobium oxide. In particular, the infiltration glass according to the invention has a solubility of <1100 µg/cm², especially <900 µg/cm² or <700 µg/cm² according to DIN EN ISO 6872.

In one embodiment of the invention, the infiltration glass according to the invention contains additions of matrix components, especially $Al_2O_3$, $CeO_2$, $Y_2O_3$ and/or $ZrO_2$.

In another embodiment, the infiltration glass according to the invention from the system $SiO_2$-$La_2O_3$—$Al_2O_3$—$B_2O_3$ with 15-35% by weight $La_2O_3$, 10-25% by weight $SiO_2$, 10-25% by weight $Al_2O_3$, 5-20% by weight $B_2O_3$, 5-20% by weight CaO, 0-10% by weight $ZrO_2$, 0-10% by weight $TiO_2$ and 0-15% by weight $CeO_2$ additionally contains $Nb_2O_5$ in an amount of from 0.1 to 20% by weight.

The infiltration glass according to the invention may contain further metal oxides at an oxidation stage suitable for the stabilization of $ZrO_2$, wherein 0-10% by weight MgO and/or 0-10% by weight $Y_2O_3$ may be admixed, in particular.

The infiltration glass according to the invention may further contain coloring oxides.

The infiltration glass according to the invention may typically be prepared and sold as a powder.

Then, the powder can be used, for example, for the infiltration of porous ceramic bodies in a per se known manner. Thus, the invention also relates to ceramic bodies infiltrated with the infiltration glass according to the invention, for example, dental restorations.

Further, the invention also relates to the use of niobium-containing glass having an $Nb_2O_5$ content of more than 0.1% by weight as an infiltration glass for all-ceramic dental compositions. In particular, $Nb_2O_5$ may be present in the infiltration glass according to the invention in amounts of from 0.1 to 20% by weight or from 5 to 15% by weight.

EXAMPLES

Example 1

A glass from the $SiO_2$—$Nb_2O_5$—$Na_2O$—$B_2O_3$ system with additions of alumina, zirconia and ceria for use for matrices of alumina and cerium-stabilized zirconia, so that no remarkable dissolution or deposition processes from the matrix into the glass or from the glass occur.

The glass with a composition of 29.5% by weight $SiO_2$, 28.7% by weight $Nb_2O_5$, 12.8% by weight $Na_2O$, 6.8% by weight $B_2O_3$, 8.0% by weight $Al_2O_3$, 6.6% by weight $ZrO_2$ and 7.6% by weight $CeO_2$ exhibits a weight loss of 3.5 mg per gram of substance after 16 hours when aged in 4% acetic acid at 80° C. The expansion coefficient $\alpha_{20\text{-}300}$ is $8.3 \cdot 10^{-6}$ $K^{-1}$, matched to a matrix of 50% by weight cerium-stabilized zirconia and 50% by weight alumina. The infiltration glass for dental all-ceramics that is employed most frequently currently (In Ceram© zirconia glass) has a weight loss of about 120 mg/g of substance.

Example 2

The glass with a composition of 29.9% by weight $SiO_2$, 37.0% by weight $Nb_2O_5$, 11.1% by weight $Na_2O$, 7.5% by weight $K_2O$, 6.7% by weight $ZrO_2$ and 7.7% by weight $CeO_2$ exhibits a weight loss of 9.2 mg per gram of substance after 16 hours when aged in 4% acetic acid at 80° C. The expansion coefficient $\alpha_{20\text{-}300}$ is $9.3 \cdot 10^{-6}$ $K^{-1}$, in this case matched to a pure cerium-stabilized zirconia matrix.

Example 3

The glass with a composition of 21.5% by weight $SiO_2$, 11.0% by weight $B_2O_3$, 17.5% by weight $Al_2O_3$, 5.5% by weight CaO, 31% by weight $La_2O_3$, 4% by weight $TiO_2$, 9.5% by weight $Nb_2O_5$ exhibits a chemical solubility of 653 μg/cm² according to DIN EN ISO 6872 after infiltration into a VITA© In-Ceram Classic ALUMINA BLANK©. In comparison, the previously commercially available VITA In-Ceram© ALUMINA GLASS POWDER exhibits a chemical solubility of about 1200 μg/cm².

The invention claimed is:

1. A ceramic body comprising a porous ceramic body and an infiltration glass comprising with niobium in quantities greater than naturally occurring quantities comprising a $SiO_2$—$Nb_2O_5$—$Na_2O/K_2O$ system with from 10 to 70% by weight $SiO_2$, from 1 to 60% by weight $Nb_2O_5$, and from 1 to 40% by weight $Na_2O/K_2O$, with the weight percentage being based on the total amount of the infiltration glass.

2. The ceramic body according to claim 1 further comprising $Al_2O_3$, $CeO_2$, $Y_2O_3$, $ZrO_2$, or a combination thereof.

3. The ceramic body according claim 1, wherein said infiltration glass further comprises metal oxides at an oxidation stage suitable for the stabilization of $ZrO_2$.

4. The ceramic body according to claim 1, wherein said infiltration glass comprises from 0 to 10% by weight MgO and/or from 0 to 10% by weight $Y_2O_3$.

5. The ceramic body according to claim 1 wherein said infiltration glass comprises coloring oxides.

6. The ceramic body according to claim 1 having a solubility of <1100 μg/cm² according to DIN EN ISO 6872.

7. The ceramic body according to claim 1, characterized in that said ceramic body is a dental restoration.

8. A method of manufacturing of a ceramic body of claim 1 comprising infiltrating the ceramic body with an infiltration glass that comprises a $SiO_2$—$Nb_2O_5$—$Na_2O/K_2O$ system with from 10 to 70% by weight $SiO_2$, from 1 to 60% by weight $Nb_2O_5$, and from 1 to 40% by weight $Na_2O/K_2O$, with the weight percentage being based on the total amount of the infiltration glass.

9. The method of claim 8 wherein the ceramic body infused with the infiltration glass provides an all-ceramic dental composition.

10. A ceramic body comprising a porous ceramic body and an infiltration glass comprising niobium in quantities greater than naturally occurring quantities comprising an addition of $Nb_2O_5$ of from 0.1 to 20% by weight to the system $SiO_2$—$La_2O_3$—$Al_2O_3$—$B_2O_3$ with 15-35% by weight $La_2O_3$, 10-25% by weight $SiO_2$, 10-25% by weight $Al_2O_3$, 5-20% by weight $B_2O_3$, 5-20% by weight CaO, 0-10% by weight $ZrO_2$, 0-10% by weight $TiO_2$ and 0-15% by weight $CeO_2$.

11. The ceramic body according claim 10, wherein said infiltration glass further comprises metal oxides at an oxidation stage suitable for the stabilization of $ZrO_2$.

12. The ceramic body according to claim 10, wherein said infiltration glass comprises from 0 to 10% by weight MgO and/or from 0 to 10% by weight $Y_2O_3$.

13. The ceramic body according to claim 10 wherein said infiltration glass comprises coloring oxides.

14. The ceramic body according to claim 10 having a solubility of <1100 μg/cm² according to DIN EN ISO 6872.

15. The ceramic body according to claim 10, characterized in that said ceramic body is a dental restoration.

16. A method of treating a ceramic body comprising infiltrating the ceramic body with an infiltration glass that comprises niobium in quantities greater than naturally occurring quantities comprising an addition of $Nb_2O_5$ of from 0.1 to 20% by weight to the system $SiO_2$—$La_2O_3$—$Al_2O_3$—$B_2O_3$ with 1535% by weight $La_2O_3$, 10-25% by weight $SiO_2$, 10-25% by weight $Al_2O_3$, 5-20% by weight $B_2O_3$, 5-20% by weight CaO, 0-10% by weight $ZrO_2$, 0-10% by weight $TiO_2$ and 0-15% by weight $CeO_2$.

17. The method of claim 16 wherein the ceramic body infused with the infiltration glass provides an all-ceramic dental composition.

18. An infiltration glass with niobium in quantities greater than naturally occurring quantities comprising an addition of $Nb_2O_5$ of from 0.1 to 20% by weight to the system $SiO_2$—$La_2O_3$—$Al_2O_3$—$B_2O_3$ with 15-35% by weight $La_2O_3$, 10-25% by weight $SiO_2$, 10-25% by weight $Al_2O_3$, 5-20% by weight $B_2O_3$, 5-20% by weight CaO, 0-10% by weight $ZrO_2$, 0-10% by weight $TiO_2$ and 0-15% by weight $CeO_2$, wherein said infiltration glass comprises coloring oxides.

* * * * *

UNITED STATES PATENT AND TRADEMARK OFFICE
CERTIFICATE OF CORRECTION

PATENT NO. : 8,349,459 B2
APPLICATION NO. : 12/532279
DATED : January 8, 2013
INVENTOR(S) : Marc Stephan and Bernhard Durschang Page 1 of 1

It is certified that error appears in the above-identified patent and that said Letters Patent is hereby corrected as shown below:

In the Claims:

Column 4, Line 38, please delete "1535%" and insert --15-35%--.

Signed and Sealed this
Fourteenth Day of May, 2013

Teresa Stanek Rea
*Acting Director of the United States Patent and Trademark Office*